US00PP33415P2

(12) United States Plant Patent
Ault

(10) Patent No.: US PP33,415 P2
(45) Date of Patent: Aug. 31, 2021

(54) ***AMSONIA* PLANT NAMED 'VERDANT VENTURE'**

(50) Latin Name: ***Amsonia ciliata* var. *tenuifolia***
Varietal Denomination: Verdant Venture

(71) Applicant: James Robert Ault, Libertyville, IL (US)

(72) Inventor: James Robert Ault, Libertyville, IL (US)

(73) Assignee: CHICAGOLAND GROWS, INC, Glencoe, IL (US)

( * ) Notice: Subject to any disclaimer, the term of this patent is extended or adjusted under 35 U.S.C. 154(b) by 0 days.

(21) Appl. No.: 17/122,725

(22) Filed: Dec. 15, 2020

(51) Int. Cl.
*A01H 5/02* (2018.01)
*A01H 6/08* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Amsonia* plant named 'Verdant Venture' that is characterized by its flower clusters that are held above the foliage and are not partially masked by the foliage, its petals that are short and broad in size, its lower growing plant habit, its narrow foliage and stems, its leaf margins that are strongly rolled inward, its stems that are finely pubescent.

2 Drawing Sheets

Botanical classification: *Amsonia ciliata* var. *tenuifolia*.
Cultivar designation: 'Verdant Venture'.

BACKGROUND OF THE INVENTION

The present invention relates to a new and distinct cultivar of *Amsonia ciliata* var. *tenuifolia* named 'Verdant Venture' and will be referred to hereafter by its cultivar name, 'Verdant Venture'. The new cultivar represents a new herbaceous perennial grown for landscape use.

The new cultivar was selected as a seedling in a trial field by the Inventor in Glencoe, Ill. The trial field was originally planted with seeds of unnamed and unpatented plants of *Amsonia ciliata* var. *tenuifolia*. Rounds of open pollination and selection occurred in 2009 and 2010 and the most compact and uniform plants were kept for further evaluation. The seeds were pooled when collected; the exact parentage of 'Verdant Venture' is therefore unknown. 'Verdant Venture' was selected as a single unique plant from the trials in October 2013.

Asexual propagation of the new cultivar was first accomplished by shoot tip cuttings by the Inventor in June of 2015 in Glencoe, Ill. Asexual propagation by shoot tip cuttings and whole shoot cuttings has determined that the characteristics of this cultivar are stable and reproduced true to type in successive generations.

SUMMARY OF THE INVENTION

The following traits have been repeatedly observed and represent the characteristics of the new cultivar. These attributes in combination distinguish 'Verdant Venture' as a unique cultivar of *Amsonia*.

1. 'Verdant Venture' exhibits flower clusters that are held above the foliage and are not partially masked by the foliage.

2. 'Verdant Venture' exhibits petals that are short and broad in size.
3. 'Verdant Venture' exhibits a lower growing plant habit.
4. 'Verdant Venture' exhibits narrow foliage and stems.
5. 'Verdant Venture' exhibits leaf margins that are strongly rolled inward.
6. 'Verdant Venture' exhibits stems that are finely pubescent.
7. 'Verdant Venture' exhibits a distinct, narrow band of white visible on the mouth of the corolla.

All of the potential seed parents of 'Verdant Venture' differ from 'Verdant Venture' in having taller plant height with more irregular plant habits and a lower proportion of flowering stems to total stems. 'Verdant Venture' can also be compared to the *Amsonia* cultivars 'Georgia Pancake' (not patented) and 'Spring Sky' (not patented). 'Georgia Pancake' is similar to 'Verdant Venture' in having threadlike foliage with rolled leaf margins and stems that are finely pubescent. 'Georgia Pancake' differs from 'Verdant Venture' in having a shorter plant height, flowers that are lighter violet-blue at anthesis with larger and more diffused white patches by the corolla throat, and an overall more open, irregular plant habit due to having nearly prostrate stems. 'Spring Sky' is similar to 'Verdant Venture' in having inflorescences that are held above the foliage and flower petals that are short in length and broad in width. 'Spring Sky' differs from 'Verdant Venture' in having stems and leaf margins that are conspicuously densely pubescent, leaf margins that are not strongly rolled, less reliable winter hardiness and lower vigor in U.S.D.A Zone 5.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Chicago Botanic Garden, University of Minnesota, Fine Gardening, and Intrinsic Perennial Gardens.

BRIEF DESCRIPTION OF THE DRAWINGS

The accompanying colored photographs illustrate the overall appearance and distinct characteristics of the new *Amsonia*. The photographs were taken of 'Verdant Venture' as grown in a trial garden in Glencoe, Ill.

The photograph in FIG. 1 provides a view of the plant habit of a 6-year-old plant of 'Verdant Venture' in peak bloom.

Figure 1:
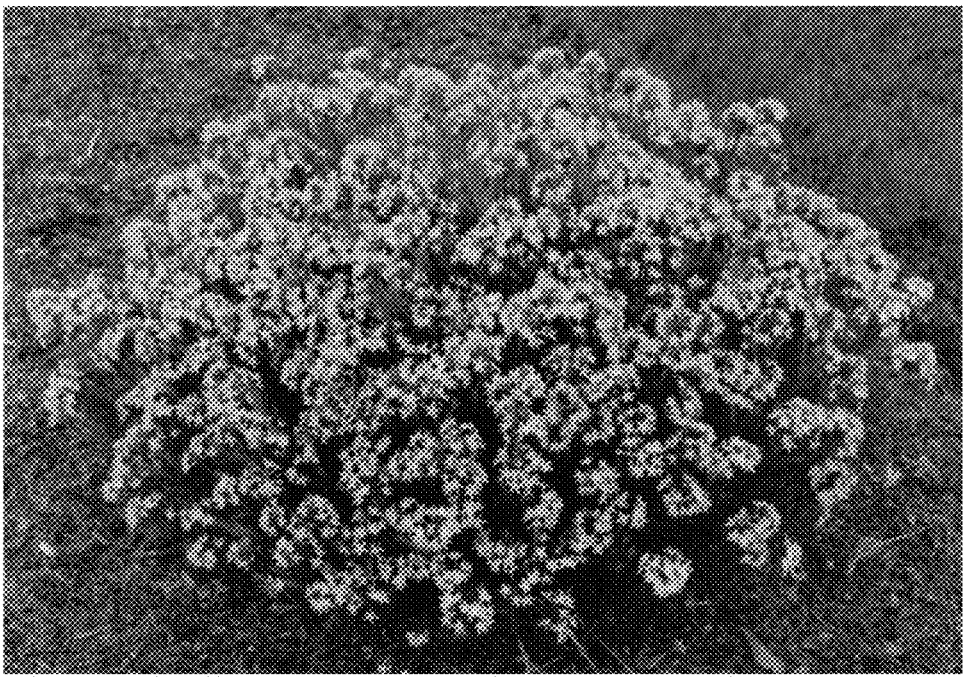
Figure 2:
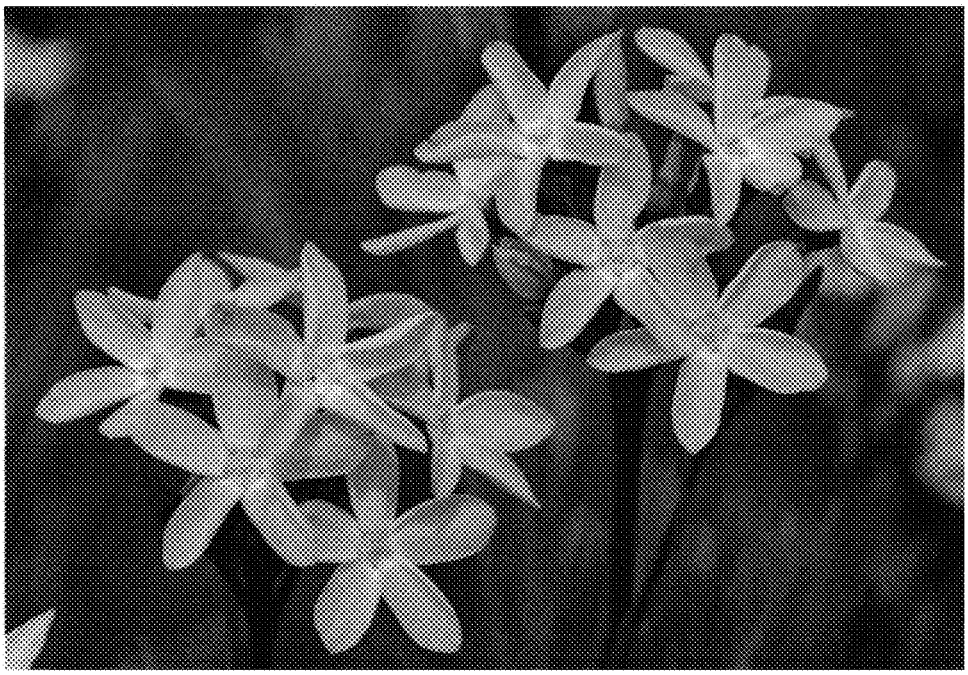

The photograph in FIG. 2 provides a close-up view of inflorescences of 'Verdant Venture'.

Figure 3:
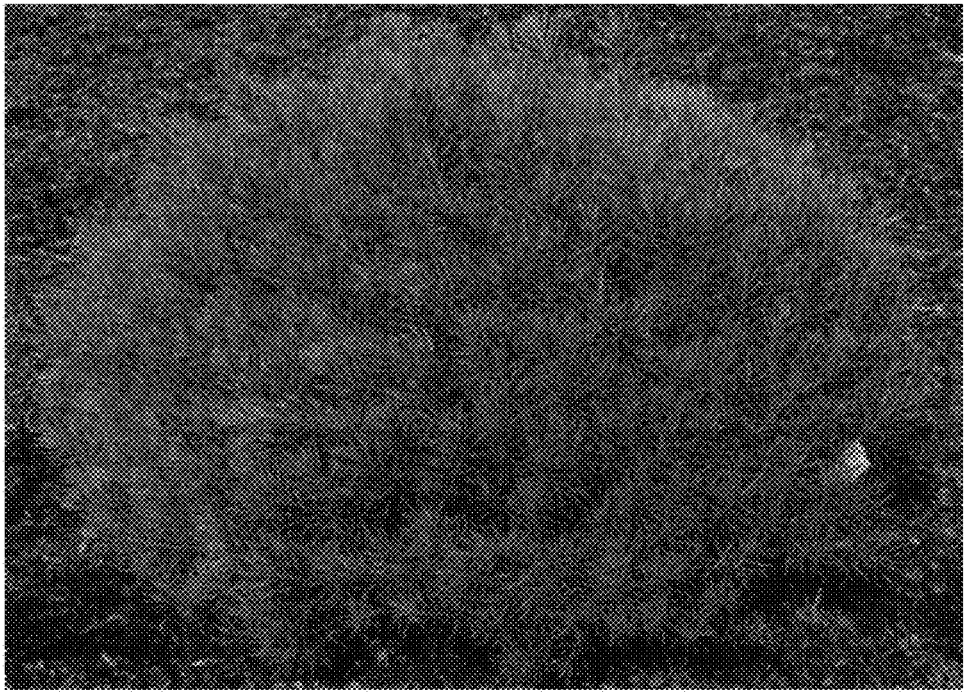

The photograph in FIG. 3 provides a view of the foliage of a 6-year-old plant of 'Verdant Venture' in summer.

Figure 4:
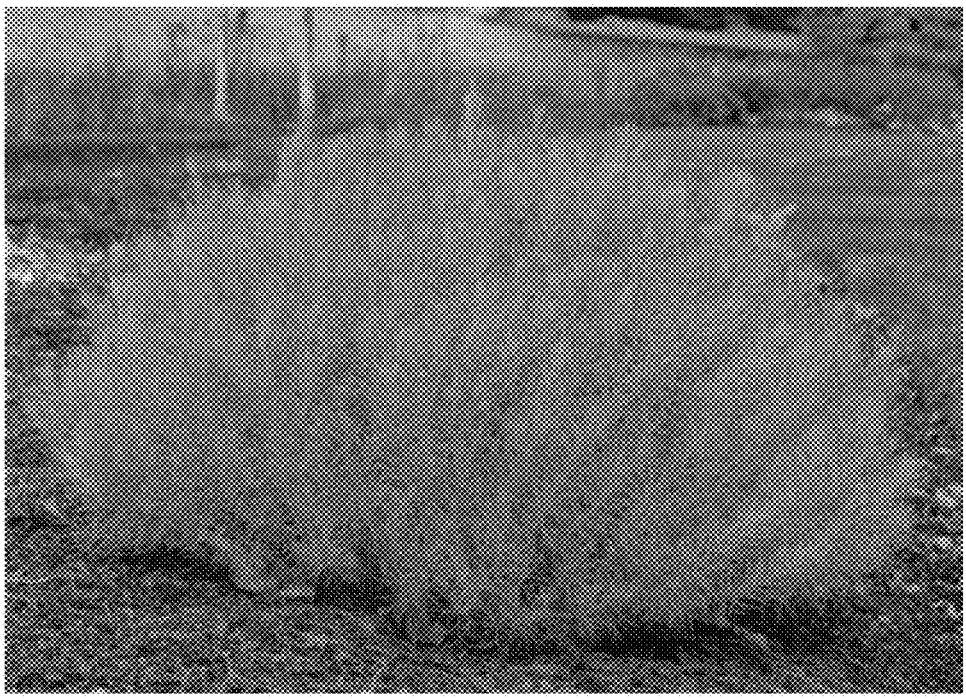

The photograph in FIG. 4 provides a view of the foliage coloration of a 5-year-old plant of 'Verdant Venture' in the fall.

The colors in the photographs are as close as possible with the photographic and printing technology utilized and the color values cited in the Detailed Botanical Description accurately describe the colors of the new *Amsonia*.

DETAILED BOTANICAL DESCRIPTION OF THE PLANT

The following is a detailed description of one-year-old plants of the new cultivar as grown in 4-inch containers in Glencoe, Ill. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Average of three weeks; commencing in early to mid-May and finishing in late May to early June in northern Illinois.

*Plant habit.*—Low-growing mound.

*Height and spread.*—Average of 32 cm in height and 17 cm in width for one-year-old potted plants, 44 cm in height and 70 cm in width for in-ground trial plants four years in age, 53 cm in height and 94 cm in width for in-ground trial plants six years in age, and 71 cm in height and 1.39 m in width for in-ground trial plants ten years in age.

*Hardiness.*—At least in U.S.D.A. Zones 4 to 8.

*Diseases and pests.*—No susceptibility or resistance to pests or diseases has been observed.

*Root description.*—Fibrous, 162A in color.

*Growth rate.*—Vigorous.

*Propagation.*—Shoot tip and entire shoot cuttings.

*Root development.*—Root initiation occurs in an average of one month and a rooted cutting will produce a plant with 3 to 5 stems in a one-quart pot in 12 months.

Stem description:

*Stem size.*—An average of 30 cm in length and 2 mm in width.

*Stem shape.*—Quadrilateral.

*Stem strength.*—Strong.

*Stem color.*—144A.

*Stem surface.*—Matte, sparsely fine pubescent.

*Stem aspect.*—Held upright to slightly outward.

*Internode length.*—An average of 4 mm.

*Branching habit.*—An average of 20 stems from base, each flowering stem producing a single inflorescence.

Foliage description:

*Leaf shape.*—Linear.

*Leaf division.*—Simple.

*Leaf base.*—Clasping.

*Leaf apex.*—Narrowly acute.

*Leaf venation.*—Parallel, inconspicuous, matches leaf color on upper and lower surfaces.

*Leaf margins.*—Entire, strongly rolled inward, no pubescence.

*Leaf attachment.*—Sessile.

*Leaf arrangement.*—Opposite and whorled.

*Leaf surface texture.*—Glabrous and dull on upper and lower surfaces.

*Leaf color* (*both surfaces*).—Young foliage; 143B, mature foliage; 143A, fall foliage; N144B to N144C and 150A to 150B.

*Leaf size.*—Up to 5 cm in length and 1.5 mm in width.

*Leaf quantity.*—An average of 120 leaves per stem.

*Leaf fragrance.*—None.

Flower description:

*Inflorescence type.*—Panicle on terminus of main stems, one per lateral branch unless pinched.

*Lastingness of inflorescence.*—About 3 to 4 weeks from the opening of the first flower to senescence of last flower, individual flower lasts about 5 days.

*Inflorescence size.*—An average of 6 cm in height and 4 cm in diameter.

*Flower fragrance.*—Light floral scent.

*Flower number.*—An average of 8 per inflorescence.

*Flower aspect.*—Upright to outward.

*Flower bud.*—Spatulate in shape, acute apex, an average of 1 cm in length and 2 mm in width, color; 92B and calyx portion 93 and 144A, surface is glabrous.

*Flower form.*—Salverform.

*Flower size.*—An average of 1.5 cm in height and diameter.

*Corolla tube.*—An average of 5 mm in length and 2 mm in width, color; N155A, outer surface glabrous, inner surface densely covered with woolly pubescence, up to 2 mm in length and NN155A in color, mouth of corolla tube visible and a distinct band of N155A.

*Corolla lobes.*—5, narrowly ovate in shape, held nearly horizontally when fully open, slightly overlapping, an average of 1 cm in length and 3 mm in width, apex bifid with a cleft 1 mm in depth and 0.5 mm in width, apex of lobes rounded, base broadly cuneate and fused to tube, entire margins, color; when opening inner and outer surfaces center portion 97D, margins 97B, tip 97A, when fully open inner and outer surface base 97D and 91D, center portion and margins 97B.

*Calyx.*—Campanulate in form, comprised of fused sepals with linear shaped sepal tips free, an average of 1 mm in length and 1.5 mm in width.

*Sepals.*—5, primarily fused with free tips, linear in shape, entire margins, fused base (about 90%), aristulate apex, an average of 2 mm in length and 0.5 mm in width, inner surface texture; glabrous and shiny, outer surface texture; glabrous and matte, 146A in color.

*Peduncles.*—Rounded in shape, an average of 2 cm in length and 1 mm in width, held upright to outward, glabrous and slightly glossy surface, 146A in color.

*Pedicels.*—Rounded in shape, an average of 1 cm in length and 1 mm in width, held upright to outward, glabrous and slightly glossy surface, 146A in color.

Reproductive organs:

*Gynoecium.*—1 pistil, 5 mm in length; stigma; rounded, N144A, style is about 4 mm in length, and NN155B in color, ovary; superior, round in shape, about 1 mm in length, 144A in color.

*Androecium.*—5 stamens; anthers; dorsifixed, heart-shaped, an average of 1 mm in length, and 202A in color, filaments; fused petals, an average of 0.5 mm in length and 155A in color, pollen is moderate in quantity and 16A in color.

*Seeds.*—None observed to date.

It is claimed:

1. A new and distinct cultivar of *Amsonia* plant named 'Verdant Venture' as herein illustrated and described.

* * * * *